(12) United States Patent
Calabresi et al.

(10) Patent No.: US 6,365,578 B1
(45) Date of Patent: Apr. 2, 2002

(54) DRUG COMINBATIONS CONTAINING AZT

(75) Inventors: Paul Calabresi; James W. Darnowski, both of Barrington, RI (US)

(73) Assignee: Roger Williams General Hospital, Providence, RI (US)

( * ) Notice: Subject to any disclaimer, the term of this patent is extended or adjusted under 35 U.S.C. 154(b) by 0 days.

(21) Appl. No.: 08/087,957

(22) Filed: Jul. 6, 1993

Related U.S. Application Data

(60) Continuation of application No. 07/740,594, filed on Aug. 5, 1991, now abandoned, which is a division of application No. 07/486,062, filed on Feb. 27, 1990, now Pat. No. 5,116,823.

(51) Int. Cl.⁷ ...................... A61K 31/70; A61K 31/495; A61K 31/50
(52) U.S. Cl. .......................................... 514/50; 514/249
(58) Field of Search .................................. 514/50, 249

(56) References Cited

U.S. PATENT DOCUMENTS

| | | | |
|---|---|---|---|
| 4,724,232 A | 2/1988 | Rideout et al. | 514/50 |
| 4,833,130 A | 5/1989 | Rideout et al. | 514/50 |
| 4,857,511 A | 8/1989 | Rideout et al. | 514/50 |

OTHER PUBLICATIONS

The Merck Index, 11ᵗʰ Ed, Merck & Co. Inc., p. 1597 (Wo 10023).*
Brunetti et al., Cancer Research, vol. 37, No. 3, 860A(1989).
Brunetti et al., Preclinical Pharmacology and Experimental Therapeutics vol. 30, 595 (Abs. 2369) (1989).
Scanlon et al., Cancer Communications, vol. 1, 269–275 (1989).
Minor et al., Proceedings of Asco, vol. 7, 4 (Abs. No. 16), (1988).
Clinical Aspects of Aids, et al., Aspects Cliniques, p. 283, M.B.P. 368, Jun. 4–9, 1989.
Physicians'Desk Reference, 46th Edition, 1992, 1217–1221.

* cited by examiner

*Primary Examiner*—Jerome D. Goldberg
(74) *Attorney, Agent, or Firm*—Fish & Richardson P.C.

(57) ABSTRACT

Combinations of 3'-azido-3'-deoxythymidine (AZT) with 5-fluorouracil (FUra) or its precursor 5-fluoro-2'-deoxyuridine (FUDR) or methoxtrexate (MTX) exhibit increased cytotoxicity and increased therapeutic index in treatment of carcinomas.

6 Claims, 3 Drawing Sheets

DRUG COMINBATIONS CONTAINING AZT

This is a continuation of application Ser. No. 07/740,594, filed Aug. 5, 1991, now abandoned, which is a divisional of 07/486,062 filed Feb. 27, 1990, which issued as U.S. Pat. No. 5,116,823 on May 26, 1992.

This invention was made with government support and the Federal government has certain rights in the invention.

This invention relates to the treatment of mammals suffering from carcinomas, and, more particularly, those suffering from human colon adenocarcinoma, and pertains more specifically to treatment to inhibit or prevent metastasis of the malignancy and/or to induce regression of tumors by the administration of medication consisting essentially of 3'-azido-3'-deoxythymidine or a pharmacologically acceptable salt thereof (AZT) as one component, in combination with a second component which is any of 5-fluorouracil (FUra) or 5-fluoro-2'-deoxyuridine (FUDR) or methotrexate (MTX).

Human colon cancer is the second most common malignancy in the United States and, when metastatic, has been an incurable disease. Chemotherapy based upon 5-fluorouracil (FUra) or its corresponding pro-drug 5-fluoro-2'-deoxyuridine (FUDR) has been the treatment of choice for the disease in its advanced stages, but objective responses have been observed only in a minority of patients, with the great majority of them lasting only a few months, as reported by Arbuck, *Cancer*, Volume 63, 1036–1044 (1989). However, both FUra and FUDR are highly toxic drugs with narrow margins of safety. MTX is also highly toxic.

It has now been found that treatment of carcinomas, with medication including both the AZT component and the second component defined above is more effective than treatment with either component alone. Not only does the combination of both components inhibit the growth of human colon tumor cells to a much greater extent than either component alone, but this is accomplished without significant increase in toxicity to the mammal as a whole, assessed by determination of mortality, changes in body weight, and changes in white blood cell counts. While applicants do not wish to be bound by a theory of operation of the combination of drug components, it is believed that the second component enhances the cytotoxicity and tissue-specificity of the AZT component, resulting both in increased effectiveness and an increased therapeutic index of the combination.

In practicing the invention, both components of the medication may be mixed together and administered simultaneously, either by intravenous or intra-arterial injection or orally where possible in any conventional carrier or vehicle such as normal saline or 5% aqueous dextrose solution, or in any other non-toxic pharmacologically acceptable vehicle or carrier. Alternatively, each component may be administered separately provided they are spaced apart by no more than about 48 hours, preferably by less than about 6 hours. In general, the less time elapsing between administration of the two components the better. In the case of separate administration, the sequence in which the components are administered is not critical, either component being administered first, although it is generally preferred that the AZT component be administered last. In the case of FUra and FUDR, administration, as is well known, is preferably by intravenous or intra-arterial injection, whereas AZT and MTX may be administered orally or by intravenous or intra-arterial injection. Each of the components may be used in any of its generally available forms, and each may be administered by any conventional procedure. However, when administered separately, the AZT component is preferably in injectable form and the second component such as FUra, can be administered by injection, e.g., intravenous or intra-arterial.

The relative proportions of the two components may be varied over a wide range from about 1 to 10 parts by weight of the AZT component, preferably from 5 to 8 parts, for each part of the second component.

The dosage may also vary over a wide range, the upper limit being generally determined by the toxicity of the second component. The toxicity of all of the components when used individually has long been known and is not greatly changed by using both components together. However, while the standard dose of AZT has been 0.4 to 0.6 g/m²/day according to the prior art, the minimum dose of AZT for humans in the present invention is 3 g/m²/day, preferably 6–9 g/m²/day or even more. In the preferred embodiment of the invention the second component is 5-fluorouracil (FUra) or its prodrug 5-fluoro-2'-deoxyuridine (FUDR) which is catabolized in vivo to FUra. In the case of FUra the dose for humans in the present invention is preferably 0.4–1 g/m²/day with a total not exceeding 1 g/m² per course of therapy regardless of the number of days over which it is spread. At least one week must be allowed as a rest period, preferably two weeks, between courses of therapy. The dose of FUDR is preferably 0.8–1 g/m²/ day for humans, and the dose of methotrexate for humans in the present invention about 0.05–0.2 g/m²/day.

The following specific examples will illustrate more fully the nature of the invention without acting as a limitation upon its scope.

EXAMPLE 1

Human colon adenocarcinoma cell line HCT-8 was cultured in sterile plastic tissue culture flasks as a monolayer in RPMI medium 1640 supplemented with 10% fetal bovine serum (both from Gibco, Grand Island, N.Y.) and passed twice weekly. Cell cultures were maintained in a humidified incubator at 37° C. in an atmosphere of 5% carbon dioxide. Under these conditions the doubling time was 18–24 hours. There were added to each of a series of 25 cubic centimeter flasks containing 10 ml each of RPMI 1640 plus 10% fetal bovine serum a specimen containing $1 \times 10^5$ HCT-8 cells. After approximately 6 hours, various concentrations of FUra either alone or in combination with 5 µM AZT, previously dissolved in media, were added to achieve concentrations of 0.5–50 µM. After 5 days cells were trypsinized, viability assessed by trypan blue exclusion, and cell number determined electronically. Cell growth inhibition was assessed by calculation of cell number as a percentage of control (no drug additive). Each determination was carried out in duplicate and repeated a minimum of three times.

Figure 1:
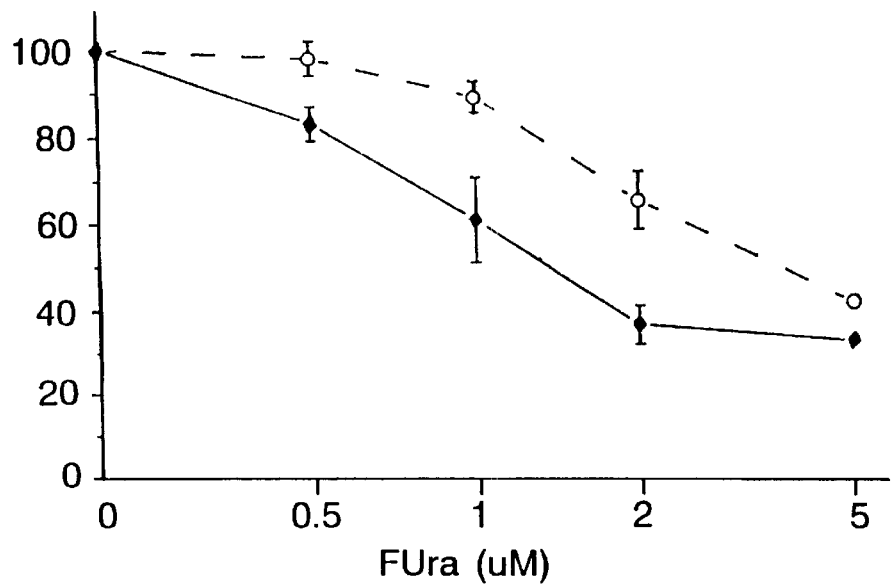
FIG. 1 is a plot showing percent decrease in number of human colon adenocarcinoma cells after 5 day (120 hour) exposure to component FUra alone.

The results are summarized in FIG. 1 of the drawing showing the combination to be more effective than FUra alone at various concentrations of FUra.

Figure 2:
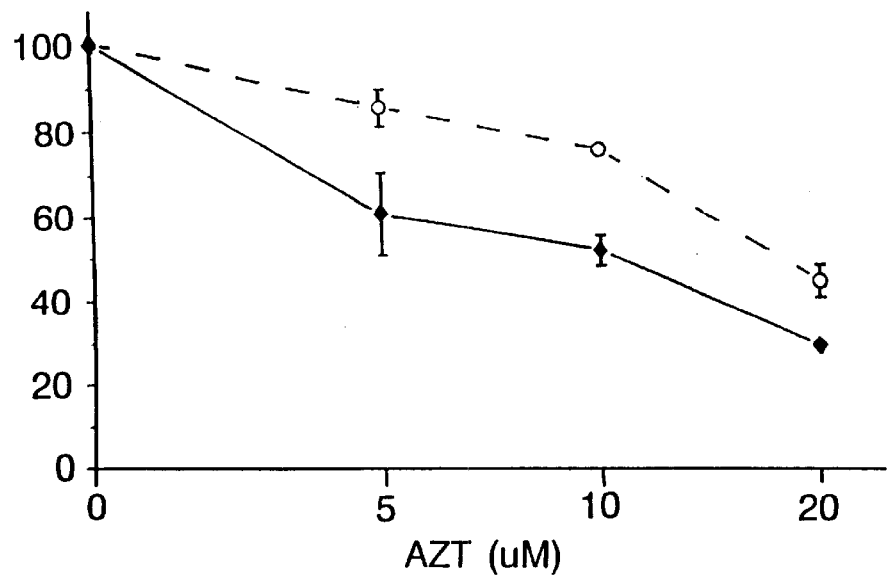
FIG. 2 is a plot showing percent decrease in number of human colon adenocarcinoma cells after 5 day (120 hour) exposure to component AZT alone as compared to its mixture with the second component (FUra)

A procedure analogous to the foregoing was carried out except that various concentrations of component AZT alone were compared with the same concentrations to which FUra at a concentration of 1 μM was added. The results are plotted in FIG. 2 of the drawing.

It is clear from the results that the combination of the AZT component with the FUra component effectively inhibited cell growth to a greater extent than either component alone.

EXAMPLE 2

In vivo tests to assess the toxicity of various dosages of AZT and FUra were carried out on Balb/C female athymic (nude) mice.

The mice were divided into groups of 5–8 animals each and treated with different doses and schedules of FUra, AZT, or both in combination. FUra and AZT were dissolved in normal saline immediately before use and were administered by intraperitoneal bolus injection so that the desired dose was contained in 0.1 ml/10 g animal body weight. FUra was administered in doses corresponding to 80, 90 and 100 mg/kg weekly or 20, 25, and 30 mg/kg for 5 consecutive days with intervening 2 week rest periods. The AZT component was administered at doses of 300 or 600 mg/kg. In those cases where the two components were not administered simultaneously, the FUra component was administered first followed in approximately 2 hours with the AZT component. Toxicity was assessed by determination of mortality, changes in body weight, and changes in white blood cell counts (WBC). Animal body weights were recorded immediately before and twice weekly after initiation of treatment and weight change was calculated as a percentage of the initial body weight. To determine WBC, blood was collected from the orbital sinus in a heparinized Natelson pipette, and after appropriate dilution the cell number was determined electronically one week after each course of therapy. The tests were carried out in duplicate and the pooled number of animals per treatment group was 10–16.

In the control group the mice received no treatment; in group 2 they received 600 mg/kg of AZT; in group 3 they received 85 mg/kg of FUra; in group 4 they received 85 mg/kg of FUra followed at a 2 hour interval by 600 mg/kg of AZT; in group 5 the mice received 100 mg/kg of FUra alone. A total of 4 courses of administration were carried out, each in triplicate, and the pooled number of animals per treatment group corresponded to 23–30. The results are shown in the following Table.

TABLE 1

| Treatment | Mortality[a] | Max weight loss[b] | WBC Nadir[b] (per mm$^3$ × 10$^3$) |
|---|---|---|---|
| Control | 0 | −7.5 ± 1.6[c] | 5.1 ± 0.2[c] |
| AZT$_{600}$ | 0 | −4.8 ± 1.9 | 4.5 ± 0.3 |
| FUra$_{85}$ | 25 | −10.2 ± 1.7 | 2.5 ± 0.2 |
| FUra$_{85}$--> AZT$_{600}$ | 29.2 | −11.9 ± 1.4 | 3.5 ± 0.3 |
| FUra$_{100}$ | 60.8 | −13.1 ± 1.8 | 1.7 ± 0.2 |

[a]Percent dead on day 29 after starting treatment
[b]As determined for individual animals during treatment
[c]Mean ± SE A second series of toxicity tests were carried out using a different regimen with similar groups of animals as follows:

Group 1 was treated with 600 mg/kg of AZT for days 3 to 5 inclusive; Group 2 was treated with 20 mg/kg of FUra from days 1 to 5; Group 3 was treated with 20 mg/kg of FUra for days 1 to 5 and with 600 mg/kg of AZT for days 3 to 5; Group 4 was treated with 25 mg/kg of FUra for days 1 to 5. The medication was administered by intraperitoneal bolus, the AZT being administered two hours after FUra. The treatment was repeated every two weeks. A total of 2 courses were administered, the tests being carried out in triplicate and the pool number of animals per treatment group corresponded to 21–30. The results are shown in the following Table.

TABLE 2

| Treatment | Mortality[a] | Max weight loss[b] | WBC Nadir[b] (per mm$^3$ × 10$^3$) |
|---|---|---|---|
| Control | 0 | −5.9 ± 1.8$_c$ | 5.7 ± 0.4[c] |
| AZT$_{600}$ | 0 | −11.3 ± 2.0 | 3.9 ± 0.4 |
| FUra$_{20}$ | 0 | −9.0 ± 1.8 | 3.3 ± 0.3 |
| FUra$_{20}$ + AZT$_{600}$ | 0 | −8.8 ± 1.5 | 2.9 ± 0.3 |
| FUra$_{25}$ | 12.5 | −12.4 ± 2.5 | 3.3 ± 0.6 |

[a]Percent dead on day 29 after starting treatment.
[b]As determined for individual animals during treatment.
[c]Mean ± SE.

EXAMPLE 3

Figure 3:
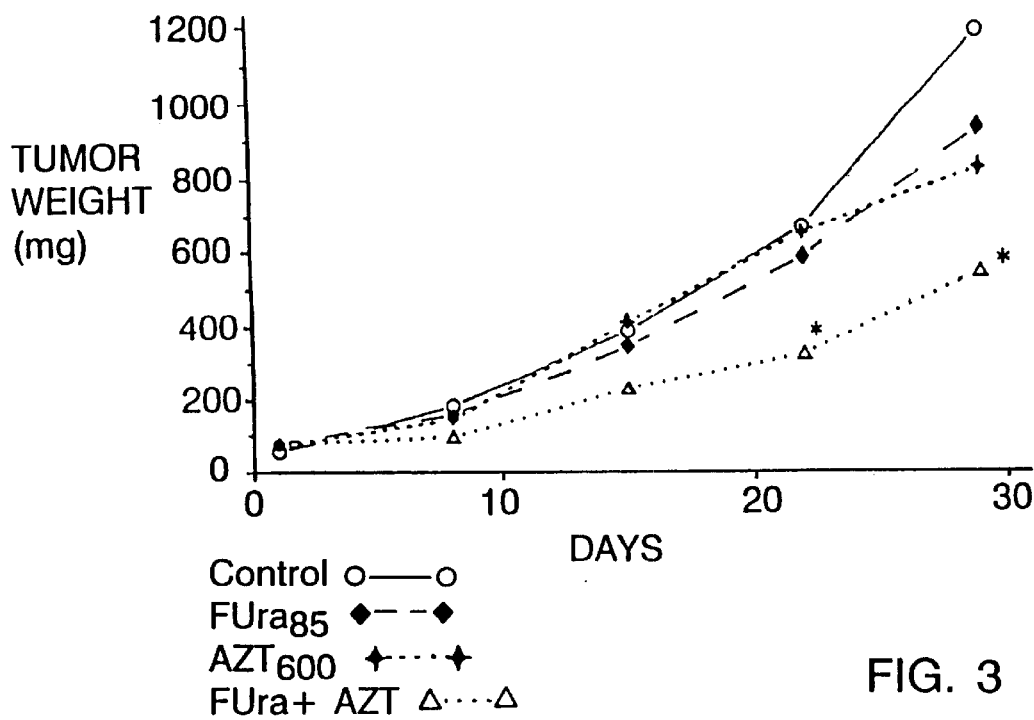
FIG. 3 is a plot showing average tumor weight of xenografts of human colon adenocarcinoma cells in nude mice treated in accordance with one embodiment of the invention.

Tests to assess therapeutic effectiveness were carried out by administering medication to groups of six- to eight-week old athymic (nude) Balb/C female mice bearing advanced (approx. 100 mg) xenografts of human colon adenocarcinoma cells (HCT-8). The medication was administered as follows:

Control group received no medication, while the remaining groups received weekly intraperitoneal doses containing, for group 1, 85 mg/kg FUra; Group 2 600 mg/kg AZT; Group 3 85 mg/kg FUra followed at 2 hours by 600 mg/kg of AZT. Each group received 4 courses of weekly regimens. The results are summarized in FIG. 3 of the drawing, in which each point represents the mean of 21 to 30 determinations; the standard error is excluded for the sake of clarity. For the points marked with an asterisk, p<0.01.

EXAMPLE 4

Figure 4:
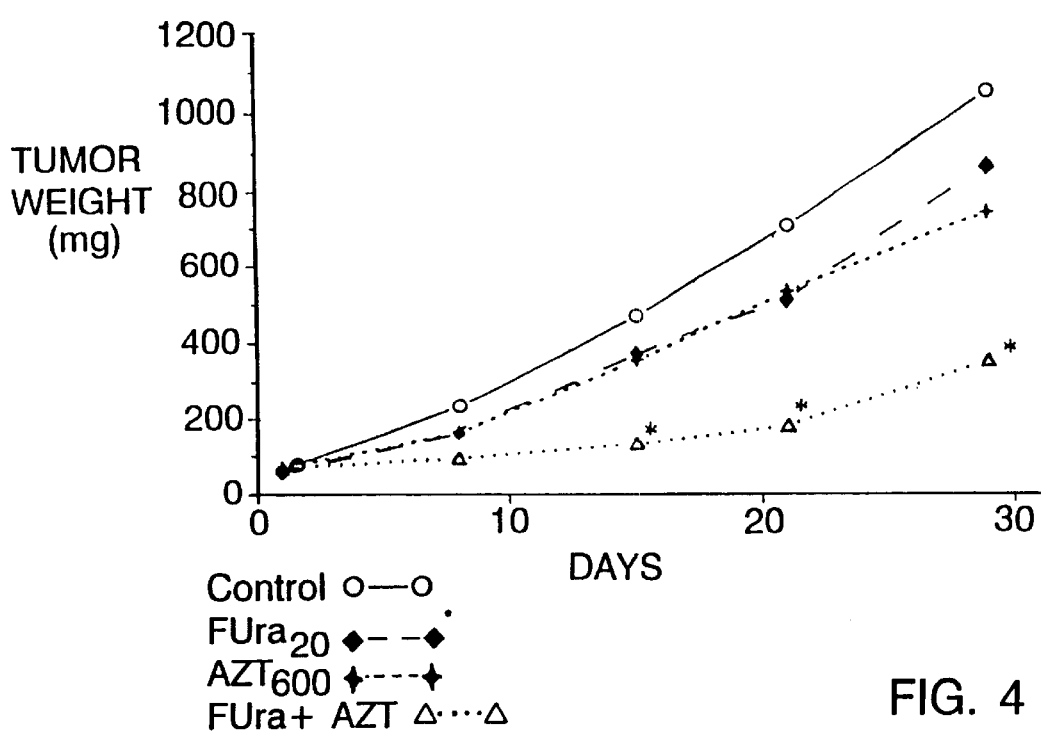
FIG. 4 is a plot similar to that of FIG. 3 showing the effect of a different dosage regimen.

Groups of mice bearing xenografts as described in Example 3 were subjected to a different regimen of treatment as follows:

Animals in the control group received no treatment, while the remaining animals received bi-weekly intraperitoneal bolus doses. Group 1 received 20 mg/kg of FUra for 5 days; Group 2, 600 mg/kg of AZT on each of days 3, 4, and 5; Group 3, 20 mg/kg of FUra for 5 days and 600 mg/kg of AZT on each of days 3, 4, and 5 administered 2 hours after the injection of FUra. The results are as shown in FIG. 4 of the drawing in which each point represents the mean of 21 to 24 determinations, the standard error being omitted for the sake of clarity. For each point marked with an asterisk, p≦ or 0.05 as compared with treatment with FUra alone.

EXAMPLE 5

Figure 5:
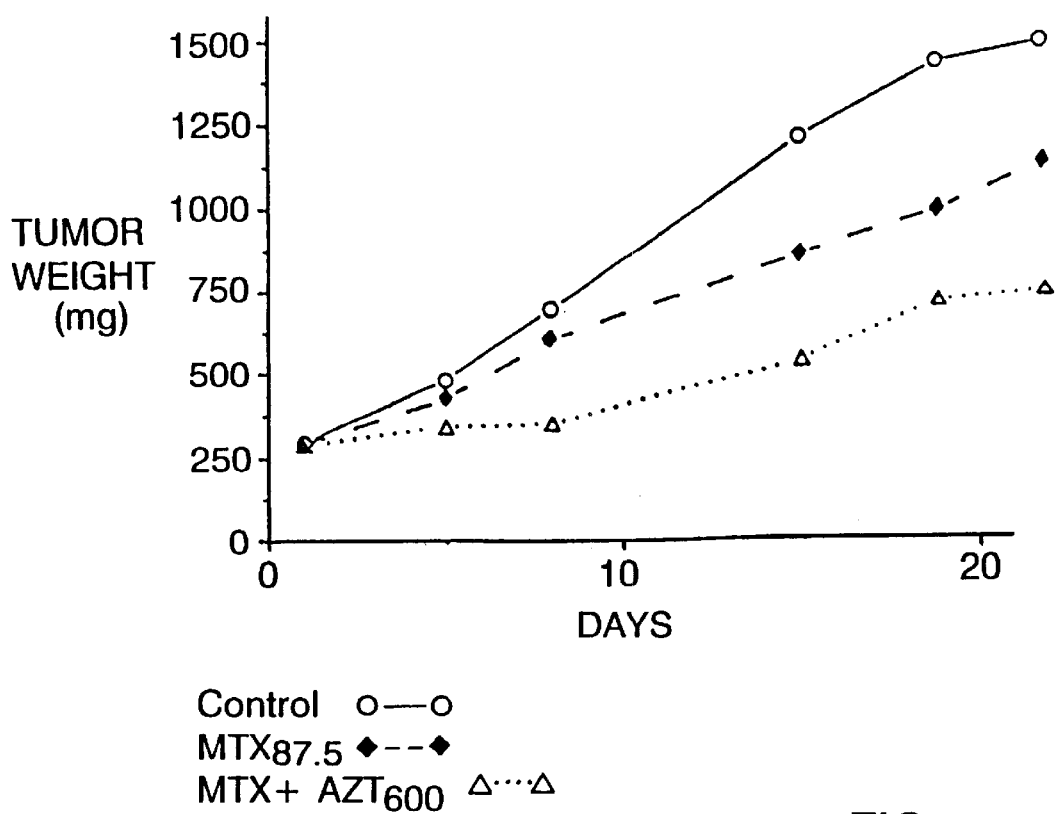
FIG. 5 is a plot similar to that of FIG. 3 showing results of treatment in accordance with a second embodiment of the invention.

Groups of mice bearing xenografts as described in Example 3 were subjected to a regimen of treatments with MTX administered at its LD$_{10}$ (87.5 mg/kg/wk) alone and also in combination with AZT (300 mg/kg) administered two hours later. The results are shown in FIG. 5 of the drawing.

Similar results can be obtained when there is substituted for the FUra an equivalent dose of 5-fluoro-2'deoxyuridine, a precursor which is rapidly catabolized to FUra in vivo upon injection. In addition, similar results have been obtained when methotrexate is substituted for FUra.

What is claimed is:

1. A method of treating a mammal suffering from carcinoma to inhibit growth of said carcinoma which comprises administering to said mammal effective doses of 3'-azido-3'-deoxythymidine and methotrexate, wherein said 3'-azido-3'-deoxythymidine and said methotrexate are administered within a 48 hour time period, and are more effective than the combined effects of separate administration of 3'-azido-3'-deoxythymidine and methotrexate.

2. A method as claimed in claim 1, in which said 3'-azido-3'deoxythymidine is administered substantially simultaneously with said methotrexate.

3. A method as claimed in claim 1 in which said 3'-azido-3'-deoxythymidine is administered separately from said MTX, said administrations being separated by no more than 6 hours.

4. A composition for treating a mammal suffering from carcinoma to inhibit growth of said carcinoma consisting essentially of 3'-azido-3'deoxythymidine in combination with methotrexate, together with a non-toxic pharmacologically acceptable carrier, said composition being more effective than the combined effects of separate administration of 3'-azido-3'-deoxythymidine and methotrexate.

5. A method of treating a mammal suffering from an adenocarcinoma to inhibit growth of said adenocarcinoma which comprises administering to said mammal effective doses of 3'-azido-3'-deoxythymidine and methotrexate, wherein said 3'-azido-3'-deoxythymidine and said methotrexate are administered within a 48 hour time period, and are more effective than the combined effects of separate administration of 3'-azido-3'-deoxythymidine and methotrexate.

6. The method of claim 5, wherein said adenocarcinoma is colon adenocarcinoma.

* * * * *